(12) United States Patent
Lin et al.

(10) Patent No.: US 6,660,510 B2
(45) Date of Patent: Dec. 9, 2003

(54) **TRANSGLUTAMINASE GENE OF *STREPTOVERTICILLIUM LADAKANUM* AND THE TRANSGLUTAMINASE ENCODED THEREFROM**

(75) Inventors: Yi-Shin Lin, Hsinchu (TW); Chang-Hsiesh Liu, Chang-Hwa (TW); Wen-Shen Chu, Hsinchu (TW)

(73) Assignee: Food Industry Research and Development, Hsonchu (TW)

( * ) Notice: Subject to any disclaimer, the term of this patent is extended or adjusted under 35 U.S.C. 154(b) by 0 days.

(21) Appl. No.: 10/022,809

(22) Filed: Dec. 17, 2001

(65) Prior Publication Data
US 2003/0113407 A1 Jun. 19, 2003

(51) Int. Cl.[7] ............................ C12N 9/10; C12N 15/00; C12N 1/20; C07H 21/04
(52) U.S. Cl. ................. 435/193; 435/252.3; 435/320.1; 435/253.5; 536/23.2
(58) Field of Search ............................. 435/193, 252.3, 435/320.1, 253.5; 536/23.2

(56) References Cited

U.S. PATENT DOCUMENTS 5,420,025 A * 5/1995 Takagi et al. ................ 435/193

OTHER PUBLICATIONS

Pasternack et al. Bacterial pro–transglutaminase from *Streptoverticillium mobaraense*. Eur. J. Biochem. 257, 570–576 (1998).*

* cited by examiner

*Primary Examiner*—Ponnathapu Achutamurthy
*Assistant Examiner*—Yong D Pak
(74) *Attorney, Agent, or Firm*—Ladas & Parry (57) ABSTRACT

The invention provides a DNA molecule encoding transglutaminase of *Streptoverticillium ladakanum*, the encoded transglutaminase and the use of the transglutaminase in industrial process.

7 Claims, 7 Drawing Sheets

```
  1  TTCGACGAGG AGAAGGGCTT CCAGCGGGCG CGTGAGGTGG CGTCCGTCAT
 51  GAACAGGGCC CTGGAGAACG CCCACGACGA GAGCGCTTAC CTCGACAACC
101  TCAAGAAGGA ACTGGCGAAC GGCAACGACG CCCTGCGCAA CGAAGACGCC
151  CGTTCCCCGT TCTACTCGGC GCTGCGGAAC ACGCCGTCCT TCAAGGAGCG
201  GAACGGAGGC AATCACGACC CGTCCAGGAT GAAGGCCGTC ATCTACTCGA
251  AGCACTTCTG GAGCGGCCAG GACCGGTCGA GTTCGGCCGA CAAGAGGAAG
301  TACGGCGACC CGGACGCCTT CCGCCCCGCC CCGGGCACCG GCCTGGTCGA
351  CATGTCGAGG GACAGGAACA TTCCGCGCAG CCCCACCAGC CCCGGTGAGG
401  GATTCGTCAA TTTCGACTAC GGCTGGTTCG GCGCCCAGAC GGAGCGGAC
451  GCCGACAAGA CCGTCTGGAC CCACGGAAAT CACTATCACG CGCCCAATGG
501  CAGCCTGGGT GCCATGCATG TCTACGAGAG CAAGTTCCGC AACTGGTCCG
551  AGGGTTACTC GGACTTCGAC CGCGGAGCCT ATGTGATCAC CTTCATCCCC
601  AAGAGCTGGA ACACCGCCCC CGACAAGGTA AAGCAGGGCT GGCC
```

```
  1  TTCGACGAGG AGAAGGGCTT CCAGCGGGCG CGTGAGGTGG CGTCCGTCAT
 51  GAACAGGGCC CTGGAGAACG CCCACGACGA GAGCGCTTAC CTCGACAACC
101  TCAAGAAGGA ACTGGCGAAC GGCAACGACG CCCTGCGCAA CGAAGACGCC
151  CGTTCCCCGT TCTACTCGGC GCTGCGGAAC ACGCCGTCCT TCAAGGAGCG
201  GAACGGAGGC AATCACGACC CGTCCAGGAT GAAGGCCGTC ATCTACTCGA
251  AGCACTTCTG GAGCGGCCAG GACCGGTCGA GTTCGGCCGA CAAGAGGAAG
301  TACGGCGACC CGGACGCCTT CCGCCCCGCC CCGGGCACCG GCCTGGTCGA
351  CATGTCGAGG GACAGGAACA TTCCGCGCAG CCCCACCAGC CCCGGTGAGG
401  GATTCGTCAA TTTCGACTAC GGCTGGTTCG GCGCCCAGAC GGAAGCGGAC
451  GCCGACAAGA CCGTCTGGAC CCACGGAAAT CACTATCACG CGCCCAATGG
501  CAGCCTGGGT GCCATGCATG TCTACGAGAG CAAGTTCCGC AACTGGTCCG
551  AGGGTTACTC GGACTTCGAC CGCGGAGCCT ATGTGATCAC CTTCATCCCC
601  AAGAGCTGGA ACACCGCCCC CGACAAGGTA AAGCAGGGCT GGCC
```

Fig. 1

```
  1 GGTACCGGCG CGGGGCGGGA AGCGGGAGTT CCTCCGCGAA GTCGAAGTCC
 51 TCCAAGGCGA GTCCAAGCGC CTTCCCTTGC CCGAGGCCAG CGCCGACCCT
101 GCTGCGTCGA TGACGGACGC AGGCGCACCG AGTCCCGCGG TCTCGCTCGC
151 CCGGAGGGGA TGCGGCGGTG TCCGGCGCCC AGCCGGATTC CGCTCCTGTG
201 ACGGAGTGGC CGGTTTTGGA GCCGTGGTGT TGCCGGGGAG TTAACTGGGA
251 GACATGATCA CTTCTCGTAG CGACCCGATC ACTCGTCCGG GAGTCGAGAA
301 GTGTTACGCC GAACCCCATT CCGCACCATC ACCCCTGCCG CCGTGACCGC
351 GGCCGGCAGT CTGCCTCTCG CCGAGAGAGC CACCCGGAGA ACCGCCCGGA
401 CGGGGTCCGC TTCACCGCTC CGGTGACGGC TTCGACGTAA CACGACCGCG
451 CCGTCACCGG CCGTATCCGG TACGCACCGC ATCCCATTC CGCCGTGCGG
501 CCGCGGCCTC TTCCTCACCG CCGTTACCGG CGCGGCACCG CAGGACGGGC
551 ACCGCCCGAC GTTATGCGCG GCCACTCGCC GCAACCTCCA CCCCCGCGT
601 CGCACTCTGG CATGCCCTCG TTCCGCGAGG TTCGCCAGAT TCAGCCCTTT
651 CGTCACGTTC GCCAAAGGAG TTGTTGTTCT TCATGTCCCA ACGCGGAGA
                                         M   S   Q   R   G   R

701 ACTCTCGTCT TCGCCGCTCT CGGTGCGGTC ATGTGCACCA CCGCGTTAAT
     T   L   V   F   A   A   L   G   A   V   M   C   T   T   A   L   M

751 GCCGTCCGCA GGCGCGGCCA CCGGCAGTGG CAGTGGCAGC GGCACCGGGG
     P   S   A   G   A   A   T   G   S   G   S   G   S   G   T   G   E

801 AAGAGAAGAG GTCCTACGCC GAAACGCACC GCCTGACGGC GGATGACGTC
     E   K   R   S   Y   A   E   T   H   R   L   T   A   D   D   V

851 GACGACATCA ACGCGCTGAA CGAAAGCGCT CCGGCCGCTT CGAGCGCCGG
     D   D   I   N   A   L   N   E   S   A   P   A   A   S   S   A   G

901 TCCGTCCTTC CGGGCCCCCG ACTCCGACGA GCGGGTGACT CCTCCCGCCG
     P   S   F   R   A   P   D   S   D   E   R   V   T   P   P   A   E

951 AGCCGCTCGA CCGGATGCCC GACCCGTACC GGCCCTCGTA CGGCAGGGCC
     P   L   D   R   M   P   D   P   Y   R   P   S   Y   G   R   A

1001 GAGACGATCG TCAACAACTA CATACGCAAG TGGCAGCAGG TCTACAGCCA
      E   T   I   V   N   N   Y   I   R   K   W   Q   Q   V   Y   S   H
```

Fig. 2A

```
1051  CCGCGACGGC AGGAAACAGC AGATGACCGA GGAACAGCGG GAGTGGCTGT
       R  D  G   R  K  Q  Q   M  T  E   E  Q  R   E  W  L  S

1101  CCTACGGTTG CGTCGGTGTC ACCTGGGTCA ACTCGGGCCA GTATCCGACG
       Y  G   C  V  G  V   T  W  V  N   S  G  Q   Y  P  T

1151  AACAGGCTGG CTTTCGCGTT CTTCGACGAG GACAAGTACA AGAACGAGCT
       N  R  L  A   F  A  F   F  D  E   D  K  Y  K   N  E  L

1201  GAAGAACGGC AGGCCCCGGT CCGGCGAAAC GCGGGCGGAG TTCGAGGGGC
       K  N  G   R  P  R  S   G  E  T   R  A  E   F  E  G  R

1251  GCGTCGCCAA GGACAGCTTC GACGAGGCGA AGGGGTTCCA GCGGGCGCGT
       V  A  K   D  S  F   D  E  A  K   G  F  Q   R  A  R

1301  GACGTGGCGT CCGTCATGAA CAAGGCCCTG GAGAACGCCC ACGACGAGGG
       D  V  A  S   V  M  N  K   A  L   E  N  A   H  D  E  G

1351  GGCGTACCTC GACAACCTCA AGAAGGAGCT GGCGAACGGC AACGACGCCC
       A  Y  L   D  N  L  K   K  E  L   A  N  G   N  D  A  L

1401  TGCGGAACGA GGATGCCCGC TCGCCCTTCT ACTCGGCGCT GCGGAACACG
       R  N  E   D  A  R   S  P  F  Y   S  A  L   R  N  T

1451  CCGTCCTTCA AGGACCGCAA CGGCGGCAAT CACGACCCGT CCAAGATGAA
       P  S  F  K   D  R  N   G  G  N   H  D  P   S  K  M  K

1501  GGCCGTCATC TACTCGAAGC ACTTCTGGAG CGGCCAGGAC CGGTCGGGCT
       A  V  I   Y  S  K  H   F  W  S   G  Q  D   R  S  G  S

1551  CCTCCGACAA GAGGAAGTAC GGCGACCCGG AGGCCTTCCG CCCCGACCGC
       S  D  K   R  K  Y   G  D  P  E   A  F  R   P  D  R

1601  GGCACCGGCC TGGTCGACAT GTCGAGGGAC AGGAACATTC CGCGCAGCCC
       G  T  G  L   V  D  M   S  R  D   R  N  I   P  R  S  P

1651  CACCAGCCCC GGCGAGAGTT TCGTCAATTT CGACTACGGC TGGTTCGGAG
       T  S  P   G  E  S  F   V  N  F   D  Y  G   W  F  G  A

1701  CGCAGACGGA AGCGGACGCC GACAAGACCG TATGGACCCA CGGCAACCAC
       Q  T  E   A  D  A  D   K  T  V   W  T  H   G  N  H

1751  TACCACGCGC CCAATGGCAG CCTGGGTGCC ATGCACGTGT ACGAGAGCAA
       Y  H  A  P   N  G  S   L  G  A   M  H  V   Y  E  S  K

1801  GTTCCGCAAC TGGTCCGACG GTTACTCGGA CTTCGACCGC GGAGCCTACG
       F  R  N   W  S  D  G   Y  S  D   F  D  R   G  A  Y  V

1851  TGGTCACGTT CGTCCCCAAG AGCTGGAACA CCGCCCCCGA CAAGGTGACA
       V  T  F   V  P  K   S  W  N  T   A  P  D   K  V  T

1901  CAGGGCTGGC CGTGATGTAA GCGGGGAGGG GAGGGGAGGC GGAGCATCCG
       Q  G  W  P
```

Fig. 2B

```
1951  GCTCCCCTCC CCACCGTCGG CTCTACAGCT CGTGGCCCGT CGTGCTGTCC

2001  ACGTGGTCCG GGATCTCGCC CTCGTGGCGG TCGCCCGTCG TCGGGGTGCC

2051  CGTGGGTTCG AACATGAGGA TGGAGGCGCC CGGGGAGGAC GGCTTGTGTT

2101  CGGTGCCCTT GGGGACCACG AAGGTGTCGC CCTTGTGGAG CCGCACAGCG

2151  CGTTCCGTGC CGTCGGGTC GCGGAGGGCG AGGTCGAAGC GGCCGTCCAG

2201  GACGAGGAAG AACTCGTCGG TGTCCTCGTG TACGTGCCAG ATGTGCTCGC

2251  CCTGGGTGTG GGCAACGCGG ATGTCGTAGT CGTTCATGCG GGCGACGATG

2301  CGCGGGCTGT AGACGTCGTC GAAGGAGGCG AGAGCCTTGG TGAGGTTGAC

2351  GGGCTCGGTG TTGTTCATGG TGTGAGTCTC GGCGGGAGGC CGCCGCGGCG

2401  TCTTGTACGT TGCTGTCACG CCTTGTTGCT GTCACGCCTT CATGAGGGCG

2451  CTCGCTCCGA AGGAGACGTC AAAGCGGTCG CACCAGATGC TGACGCTGGT

2501  GTAGCGGTCG AGGTCCAGGT CCCGTGGGAG GGCGTAGTTC TGGTCGCCCT

2551  TGTTGCCTTT CAGGGAGCCG AGACTGACGT GGGCGCCGTC GTCGAAGACG

2601  TGCCAGCCGG CACGGCCCGG TTTCACCGGT GCGTCGCTGA GGAGGACCTT

2651  CACGTCCGGG CCGTTGCTCG TGTCGAGGCC CTCCAGGCGG AGGGTGCGGC

2701  TGCCGTCCGG GAGGCGGAGG ACGCGGACGG TGCCGGAGGT GGTGTGTTCG

2751  TGGCTGATGA GGGTGCCCGT GGCCAGGGTG CGGGTGGCGG CGGTGGGCGC
```

Fig. 2C

```
2801  CGCCTCGTGG ACCGTCTCGT TCTGCCACAG CTTCCACGGC TGGAACCAGT

2851  AGGCCGCCAC TCCGGCCGCC AGGACCGCGA CGCCCAGCGC CCCGGCGGCG

2901  AACGGCCGCC GCCACCACCG TCGTACCTGT ACGTGCACCA CTGTCCGTCT

2951  CCCGTCGTCT CGCGCCATCC GGACCTGTAT GAAGCGCAAC GTCCGGGGCG

3001  GCCGGATTTC TCCCACAACC GGCACGGCCA CGGGATCAGT GCGTCACGGC

3051  AGCACCGCCA CCCCGTCCAG TTCACCAGT GCCTCCCCGT CCCACAGCCG

3101  CACCGCGCCG ATCACCGCCA TCGCCGGGTA GTCCGCCCC GCCAGCCGCC

3151  GCCAGACGCG GCCCAGCTCC CCGGCGCACG CGCGGTACGC CGCGACGTCC

3201  GTCGTGTAGA CCGTGACGCG GGCGAGGTCG GCCGGGGTAC C
```

TRANSGLUTAMINASE GENE OF STREPTOVERTICILLIUM LADAKANUM AND THE TRANSGLUTAMINASE ENCODED THEREFROM

BACKGROUND OF THE INVENTION

1. Field of the Invention

The present invention relates to a novel DNA molecule encoding transglutaminase and the transglutaminase encoded therefrom.

2. Description of the Prior Art

Transglutaminases are $Ca^{2+}$-dependent enzymes that catalyze the formation of isopeptide bonds in proteins between the side chain gamma-carboxamide group of glutamine and the side chain epsilon-amino group of lysine. The transglutaminases can be used in food processing such as the production of gelatinous, crosslinked gel, the induction of crosslinking of the surface of a fiber bundle and the production of cheese product. The transglutaminases also can be used in the treatment of chronic wound condition and as biological glues.

Transglutaminases have been found both extracellularly and intracellularly. A wide variety of transglutaminases have been identified and characterized from a number of animals and a few plant species. Unfortunately, transglutaminases derived from animals, such as guinea pigs, is impractical for use in industry because it is difficult to obtain a large amount of such animal-derived transglutaminases at low costs. Only few microbial transglutaminases have been disclosed, namely tranglutaminases from the species *Streptoverticillium mobaraense, Streptoverticillium cinnamoneum,* and *Streptoverticillium griseocarneum* (in U.S. Pat. No. 5,156, 956) and from the species contemplated to be *Streptomyces lavendulae* (in U.S. Pat. No. 5,252,469). According to Wu et al, the transglutaminases of *Streptoverticillium ladakanum* has the highest activity among the strains screened (Wu et al., 1996, Chinese Agric. Chem. Soc. 34(2): 228–40).

The genes encoding transglutaminase have been cloned from Streptoverticillium sp. S-8112 (Washizu et al., 1994, Biosci. Biotechnol. Biochem. 58(1): 82–7.), *Streptoverticullium cinnamoneum* (Pasternack et al., 1998, Eur.J. Biochem. 257(3): 570–6.), *Streptomyces lydicus* (WO 9,606,931), and *Bacillus subtilis* (Kobayashi et al., 1998, J. Gen. Appl. Microbiol. 44: 85–91).

Incidentally, current genetic engineering techniques have made it possible to obtain a large amount of an enzyme relative easily. This is achieved by isolating the gene coding for the enzyme, determining the base sequence of the enzyme, producing a recombinant DNA containing the gene coding for the enzyme, incorporating the recombinant DNA into microorganism or animal or plant cells, and cultivating the obtained transformants.

SUMMARY OF THE INVENTION

One object of the invention is to provide an isolated and purified DNA molecule comprising a sequence encoding transglutaminase, wherein said nucleic acid hybridizes under highly stringent conditions to the sequence as shown in SEQ ID NO: 1, or the complements thereof.

Another object of the invention is to provide an expression vector comprising the DNA molecule of the invention.

One further object of the invention is to provide a host cell comprising the expression vector of the invention.

Another further object of the invention is to provide a polypeptide comprising the amino acid sequence encoded by the DNA molecule of the invention.

BRIEF DESCRIPTION OF THE DRAWINGS

FIGS. 2A–D show the 3241-nucleotide sequence of the KpnI fragment (SEQ ID NO: 9) gene of SEQ ID NO: 1 at around nucleotides 700 to 1900 of the second open reading frame of the KpnI fragment.

DETAILED DESCRIPTION OF THE INVENTION

The present invention features a novel DNA molecule encoding transglutaminase obtained from *Streptoverticillium ladakanum*. Moreover, the invention provides a construct to express the encoded transglutaminase with high activity.

Definitions

The terms "isolated and purified", as used herein, refer to in vitro isolation of a DNA molecule or protein from its natural cellular environment, and from association with other coding regions of the bacterial genome, so that it can be sequenced, replicated, and/or expressed. Preferably, the isolated and purified DNA molecules of the invention comprise a single coding region. Although the DNA molecule includes a single coding region, it can contain additional nucleotides that do not detrimentally affect the function of the DNA molecule. For example, the 5' and 3' untranslated regions may contain variable numbers of nucleotides. Preferably, additional nucleotides are outside the single coding region.

The term "amino acid sequence", as used herein, refers to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. Amino acid sequence includes an oligopeptide, peptide, polypeptide, or protein sequence, and fragments or portions thereof, and to naturally occurring or synthetic molecules.

The term "deletion", as used herein, refers to a change in either amino acid or nucleotide sequence in which one or more amino acid or nucleotide residues, respectively, are absent.

The term "insertion" or "addition", as used herein, refers to a change in an amino acid or nucleotide sequence resulting in the addition of one or more amino acid or nucleotide residues, respectively, as compared to the naturally occurring molecule.

The term "vector", as used herein, refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome.

The term "host cell", as used herein, refers to a cell of a host which can be infected with a vector, such as a palsmid.

The hosts suitable for the invention include those commonly and conventionally used in the art.

Nucleic Acids

One object of the invention is to provide an isolated and purified DNA molecule comprising a sequence encoding transglutaminase, wherein said nucleic acid hybridizes under highly stringent conditions to the sequence as shown in SEQ ID NO: 1, or the complements thereof. More preferably, said DNA molecule encodes transglutaminase having an amino acid sequence shown in SEQ ID NO: 2. Most preferably, said DNA molecule is represented by the complete nucleotide sequence shown in SEQ ID NO: 1.

Nucleic acids having sequence similarity are detected by hybridization under highly stringent conditions. The highly stringent hybridization condition refers to hybridization in buffer containing 0. for example, at hybridization in buffer containing 0.25 M Na2HPO4 (pH 7.4), 7% sodium dodecyl sulfate (SDS), 1% bovine serum albumin (BSA), 1.0 mM ethylene diamine tetraacetic acid (EDTA, pH 8) at 65.degree. C., followed by washing 3.times. with 0.1% SDS and 0.1.times.SSC (0.1.times.SSC contains 0.015 M sodium chloride and 0.0015 M trisodium citrate, pH 7.0) at 65 degree. C.

The sequence encoding transglutaminase of the invention may be mutated in various ways known in the art to generate targeted changes in promoter strength, sequence of the encoded protein, etc. The DNA sequence or product of such a mutation will be substantially similar to the sequences provided herein, i.e. They will differ by at least one nucleotide amino acid, respectively, and may differ by at least two but not more than about ten nucleotides or amino acids. The changes may be substitutions, insertions or deletions.

Several different methods are available for isolating DNA of the invention. These include, for example, purifying enzyme protein, and then subjecting it to amino acid microsequencing, either directly or after limited cleavage. The obtained partial amino acid sequence can be used to design degenerate oligonucleotide probes or primers for use in the generation of unique, nondegenerate nucleotide sequences by polymerase chain reaction (PCR), sequences that can in turn be used as probes for screening DNA libraries. Antibodies raised against purified protein may also be used to isolate DNA clones from DNA expression libraries. Alternatively, the sequences of DNA molecules for related enzymes may be used as starting points in a cloning strategy. This method is often referred to as "cloning by homology." Another way of utilizing sequence information from different species is to take advantage of shorter areas of high sequence homology among related DNA molecules from different species and to perform the polymerase chain reaction sequencing amplification method (PCR) to obtain "species-specific" nondegenerate nucleotide sequences. Such a sequence can then be used for DNA library screening or even for direct PCR-based DNA cloning.

Using standard biochemical procedures well-known in the art, oligonucleotide probes can be used to detect and amplify a DNA molecule of the invention in a wide variety of samples. For example, Southern or Northern blotting hybridization techniques with labeled probes can be used. Alternatively, PCR techniques can be used, and nucleic acid sequencing of amplified PCR products can be used to detect mutations in the DNA.

Expression Vector and Host System

Figure 1:
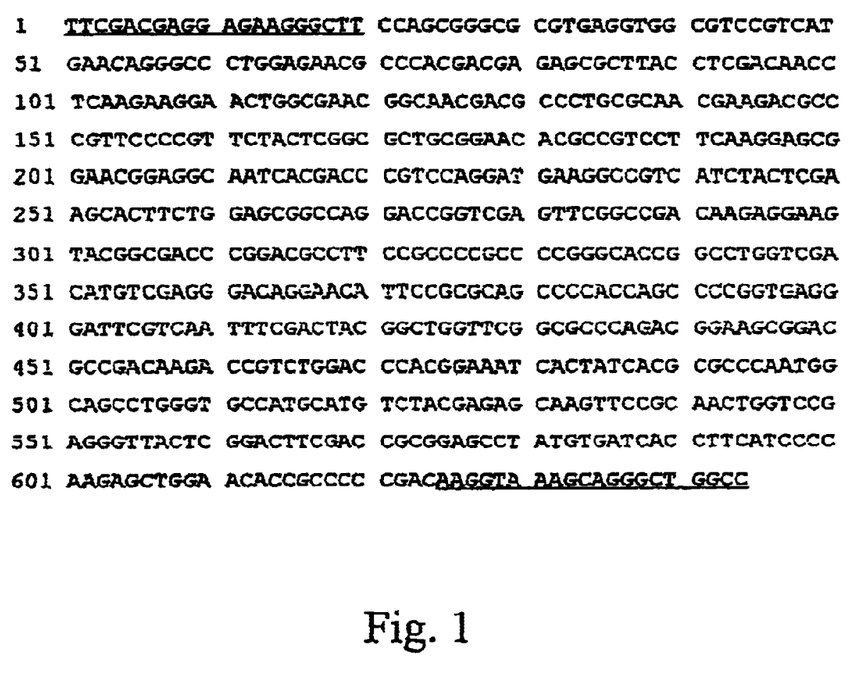
FIG. 1 shows partial fragment (644 bp) of transglutaminase gene of *S. mobaraense* CCRC 12165 (SEQ ID NO: 3).
Figure 2A:
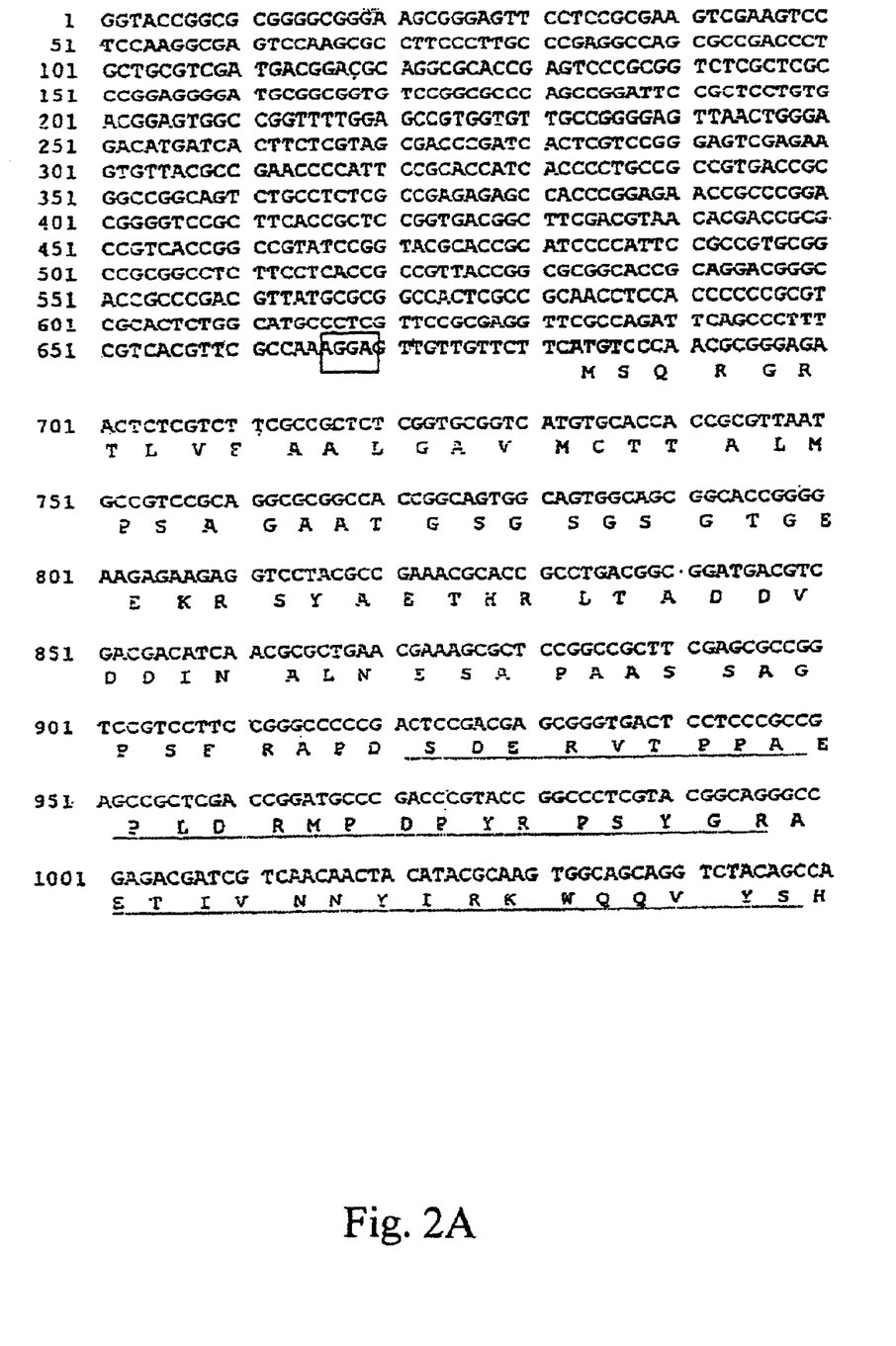
Figure 2C:
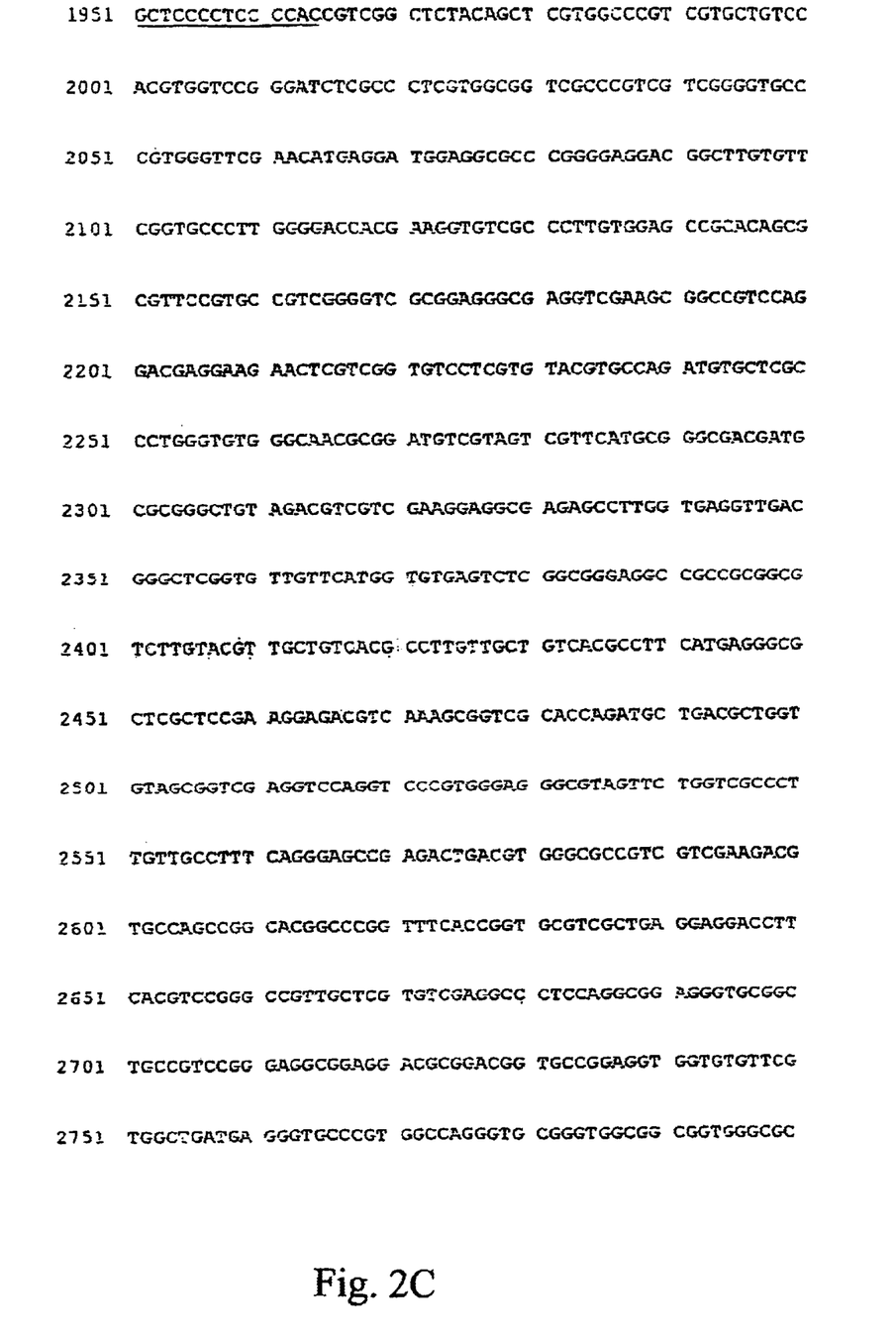
Figure 2D:
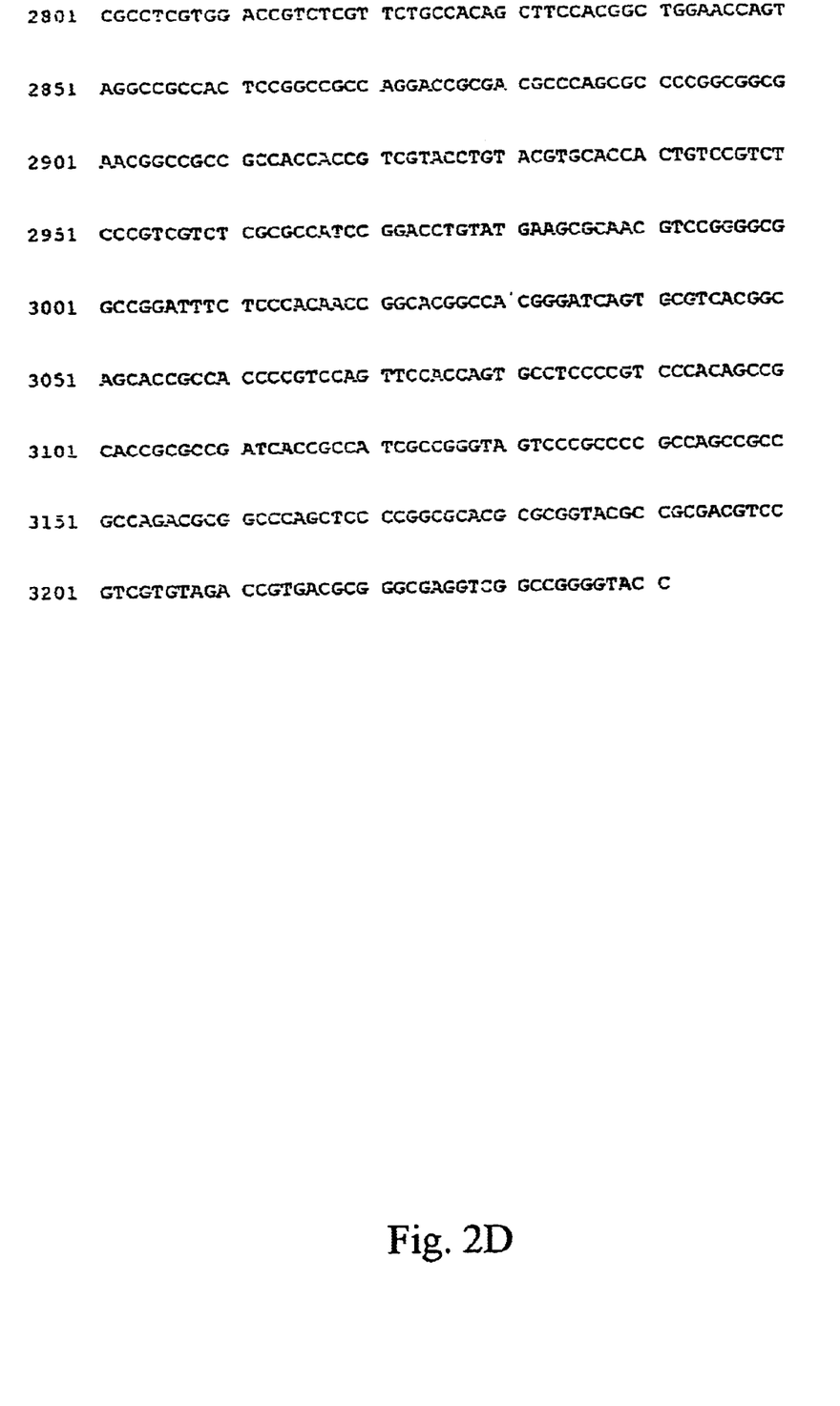

Another object of the invention is to provide an expression vector containing the DNA molecule as shown in SEQ ID NO: 1. In order to express a biologically active transglutaminase, the nucleic acid sequences encoding transglutaminase, may be inserted into appropriate expression vector, i.e., a vector which contains the necessary elements for the transcription and translation of the inserted coding sequence. According to the invention, the methods well known to those skilled in the art may be used to construct expression vectors containing the DNA molecule as shown in FIG. 1 and appropriate transcriptional and translational control elements. These methods include in vitro recombinant DNA techniques, synthetic techniques, and in vivo genetic recombination.

Another object of the invention is to provide a host cell containing the expression vector containing the DNA molecule as shown in SEQ ID NO: 1. According to the invention, a number of host systems may be utilized to contain and express sequences encoding transglutaminase. These include, but are not limited to, microorganisms, such as bacteria, transformed with recombinant bacteriophages, plasmids, or cosmid DNA expression vectors; yeasts transformed with yeast expression vectors; insect cell systems infected with virus expression vectors; plant cell systems transformed with virus expression vectors or with bacterial expression vectors; or animal cell systems. Preferably, the vectors are transformed to *Streptomyces lividans* to express transglutaminase.

Polypeptides

Another object of the invention is to provide a polypeptide, comprising the amino acid sequence encoded by the DNA molecule as shown in SEQ ID NO: 1. Preferably, the polypeptide comprises the amino acid sequence as shown in SEQ ID NO: 2.

The polypeptides of the invention may be available in a large amount. By employing an expression host, the protein may be isolated and purified in accordance with conventional ways. A lysate may be prepared of the expression host and the lysate purified using HPLC, exclusion chromatography, gel electrophoresis, affinity chromatography, or other purification techniques. The purified protein will generally be at least about 80% pure, preferably at least about 90% pure, and may be up to 100% pure. Pure is intended to mean free of other proteins and cellular debris.

Utility

The DNA molecule of the invention can be used in encoding the transglutaminase. The DNA molecule is largely expressed to produce transglutaminase in large amounts. The resulting transglutaminase has the use in a variety of industrial purposes, including gelling of proteins; improvement of baking quality of flour; producing paste type food or food ingredients from protein, fat and water; preparation of cheese from milk concentrate; binding of chopped meat or fish products; improvement of taste and texture of food proteins; casein finishing in leather processing; shoe shine, etc.

The following Examples are offered by way of illustration and not by way of limitation.

EXAMPLES

Example 1

Transglutaminase Gene of *S. ladakanum*

A. Cloning of Transglutaminase Gene of *S. ladakanum*

(1) PCR Amplification and Purification of the Transglutaminase Gene Fragment of *S. mobaraense*

Degeneracy primers were designed according to the two amino acid fragments FDEEKGF and KVKQGWP, which are the regions of the lowest degeneracy levels in the transglutaminase amino acid sequence of Streptoverticillium S-8112 cloned by Washizu et al. in 1994 (Washizu, K. et al., Biosci. Biotechnol. Biochem. 58 (1): 82–7). The two degeneracy primers are:

5'-aaaaacctgaaaccctt(ct)ga(ct)ga(ag)ga(ag)aa(ag)gg(gact)tt-3' and

5'-cttatcaacggatacggcca(gatc)cc(tc)tg(tc)tt(gact)ac(tc)tt-3'.

The Two Nested-primers are:

5'-aaaaacctgaaaccc-3' and

5'-cttatcaacggatac-3'.

The partial fragment of transglutaminase gene of *S. mobaraense* CCRC 12165 was amplified and purified by nested-PCR. The result showed a DNA band at around 650 bp, which corresponds to the calculated length of the PCR product (644 bp). The sequence of the resulting DNA is shown in FIG. 1 (SEQ ID NO. 3). The *S. mobaraense* CCRC 12165 is listed in the catalog of Culture Collection and Research Center, Food Industry Research and Development Institute (FIRDI), Hsinchu, Taiwan, ROC.

(2) Probing the complete transglutaminase gene of *S. ladakanum* by using the partial transglutaminase gene fragment of *S. mobaraense* as a probe The 644-bp DNA was used as a probe for the Southern Blotting Experiment. Signals were detected in the following restriction enzyme cut fragments of the *S. ladakanum* genome: 8.4-kb BamHI DNA, 6-kb BclI DNA, 9-kb NcoI DNA and 7.5-kb PstI DNA. The *S. ladakanum* is listed in catalog (accession number CCRC 12422) of Culture Collection and Research Center, Food Industry Research and Development Institute (FIRDI), Hsinchu, Taiwan, ROC.

In order to purify said DNA fragments comprising the transglutaminase gene, the *S. ladakanum* genome DNA was cut by NcoI and separated by electrophoresis. The purified 9-kb DNA was inserted into a pMTL23 vector cut by NcoI and transformed into *Escherichia coli* DH5α to form a DNA library. The above 644-bp DNA was used again as a probe for the colony hybridization experiment, and recombinant vectors comprising the transglutaminase gene of *S. ladakanum* were selected. Since the NcoI fragment was too big for sequencing, a 3.2-kb KpnI fragment comprising the transglutaminase gene was cloned and inserted into the KpnI cutting site on the pMT23 vector (to become pAE021) and then was sequenced. The 3241-nucleotide sequence of the KpnI fragment is shown in FIGS. 2A–D. Said sequence was analyzed by the codonpreference software provided by GCG, and a gene was predicted to be at around nucleotides 700 to 1900 of the sequence of KpnI fragment (FIGS. 2A–D). Said gene is the transglutaminase gene of *S. ladakanum*. The amino acid sequence proposed from the above nucleotide sequence is also shown in FIGS. 2A–D, which consists of 410 amino acids and the molecular weight thereof is 45780.2 Daltons. The mature transglutaminase of *S. ladakanum* is proposed to start from amino acid 80 and consist of 331 amino acids (the underlined region in FIGS. 2A–D), with a molecular weight of 37922.3 Daltons and an isoelectric point of 7.07.

Figure 3:
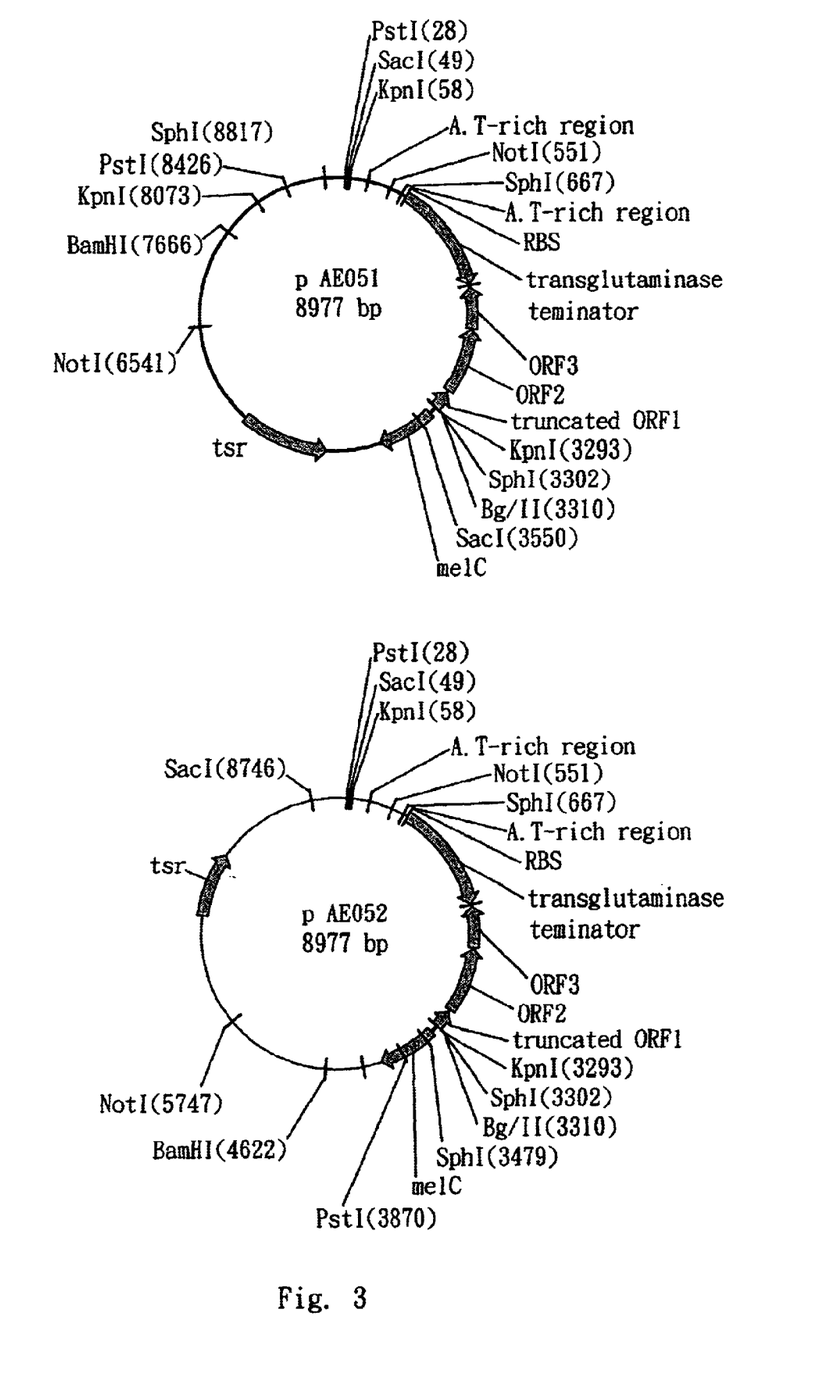
FIG. 3 shows the restriction maps of plasmids pAE051 and pAE052.
Figure 4:
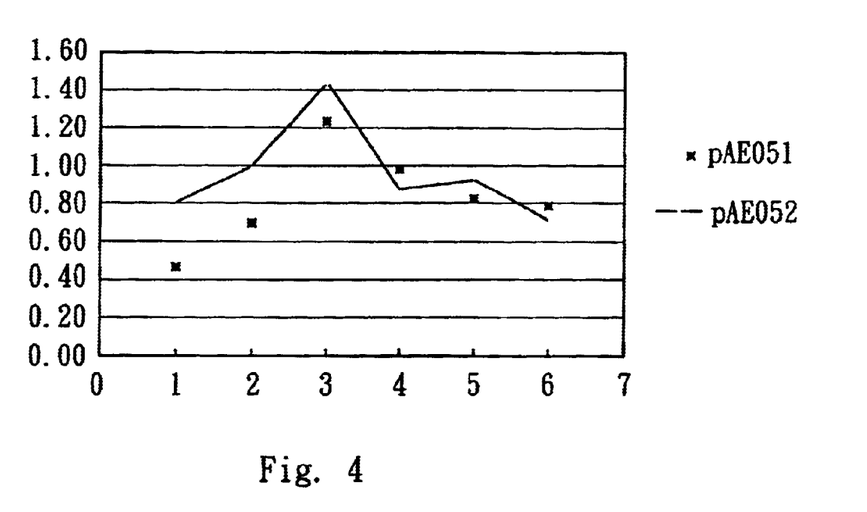
FIG. 4 shows the expression activity of plasmid pAE051 in *S. lividans* JT46.

B. Expressing the Transglutaminase Gene of *S. ladakanum* in *S. lividans* pAE021 was cut by BglII and BamHI. The resulting 3.2-kb DNA fragment comprising the transglutaminase gene was purified and inserted into the BglII cutting site on pIJ702 to become pAE051 and pAE052 (A and B of FIG. 3). pAE052 was expressed in *S. lividans* JT46 and the activity of transglutaminase in the supernatant was measured every 24 hours. The transformed clone has maximum transglutaminase activity of 1.46 U/ml at the 72th hour (FIG. 4). *S. ladakanum* transglutaminase specific antibody analysis of the extracellular culture medium has detected both mature and unmodified or partial modified transglutaminase, with the molecular weight thereof distributed between 45.8 kD and 38 kD. The above results showed that *S. lividans* JT46 expressed transglutaminase in a large amount.

What is claimed is:

1. An isolated and purified DNA molecule comprising a nucleotide sequence encoding a transglutaminase having the amino acid sequence of SEQ ID NO: 2.

2. An isolated and purified DNA molecule comprising the nucleotide sequence of SEQ ID NO: 1.

3. An expression vector comprising the DNA molecule of claim 1.

4. An expression vector comprising the DNA molecule of claim 2.

5. A host cell, which is *Streptomyces lividans,* comprising a vector which comprises a nucleotide sequence encoding a transglutaminase having the amino acid sequence of SEQ ID NO: 2 or an amino acid sequence that differs from the amino acid sequence of SEQ ID NO: 2 by not more than about 10 amino acids.

6. A host cell, which is *Streptomyces lividans,* comprising the expression vector of claim 3.

7. A host cell, which is *Streptomyces lividans,* comprising the expression vector of claim 4.

* * * * *

UNITED STATES PATENT AND TRADEMARK OFFICE
CERTIFICATE OF CORRECTION

PATENT NO. : 6,660,510 B2  Page 1 of 1
DATED : December 9, 2003
INVENTOR(S) : Yi-Shin Lin et al.

It is certified that error appears in the above-identified patent and that said Letters Patent is hereby corrected as shown below:

<u>Title page,</u>
Item [73], Assignee, after "Development" insert -- Institute -- and "Hsonchu" should read -- Hsinchu --.

Signed and Sealed this

Second Day of March, 2004

JON W. DUDAS
*Acting Director of the United States Patent and Trademark Office*

SEQUENCE LISTING

<160> NUMBER OF SEQ ID NOS: 5

<210> SEQ ID NO 1
<211> LENGTH: 1233
<212> TYPE: DNA
<213> ORGANISM: Streptoverticillum ladakanum
<220> FEATURE:
<221> NAME/KEY: CDS
<222> LOCATION: (1)..(1230)
<223> OTHER INFORMATION:

<400> SEQUENCE: 1

```
atg tcc caa cgc ggg aga act ctc gtc ttc gcc gct ctc ggt gcg gtc         48
Met Ser Gln Arg Gly Arg Thr Leu Val Phe Ala Ala Leu Gly Ala Val
1               5                   10                  15 atg tgc acc acc gcg tta atg ccg tcc gca ggc gcg gcc acc ggc agt         96
Met Cys Thr Thr Ala Leu Met Pro Ser Ala Gly Ala Ala Thr Gly Ser
            20                  25                  30 ggc agt ggc agc ggc acc ggg gaa gag aag agg tcc tac gcc gaa acg        144
Gly Ser Gly Ser Gly Thr Gly Glu Glu Lys Arg Ser Tyr Ala Glu Thr
        35                  40                  45 cac cgc ctg acg gcg gat gac gtc gac gac atc aac gcg ctg aac gaa        192
His Arg Leu Thr Ala Asp Asp Val Asp Asp Ile Asn Ala Leu Asn Glu
    50                  55                  60
```

-continued

```
agc gct ccg gcc gct tcg agc gcc ggt ccg tcc ttc cgg gcc ccc gac    240
Ser Ala Pro Ala Ala Ser Ser Ala Gly Pro Ser Phe Arg Ala Pro Asp
65              70                  75                  80 tcc gac gag cgg gtg act cct ccc gcc gag ccg ctc gac cgg atg ccc    288
Ser Asp Glu Arg Val Thr Pro Pro Ala Glu Pro Leu Asp Arg Met Pro
                85                  90                  95 gac ccg tac cgg ccc tcg tac ggc agg gcc gag acg atc gtc aac aac    336
Asp Pro Tyr Arg Pro Ser Tyr Gly Arg Ala Glu Thr Ile Val Asn Asn
            100                 105                 110 tac ata cgc aag tgg cag cag gtc tac agc cac cgc gac ggc agg aaa    384
Tyr Ile Arg Lys Trp Gln Gln Val Tyr Ser His Arg Asp Gly Arg Lys
        115                 120                 125 cag cag atg acc gag gaa cag cgg gag tgg ctg tcc tac ggt tgc gtc    432
Gln Gln Met Thr Glu Glu Gln Arg Glu Trp Leu Ser Tyr Gly Cys Val
130                 135                 140 ggt gtc acc tgg gtc aac tcg ggc cag tat ccg acg aac agg ctg gct    480
Gly Val Thr Trp Val Asn Ser Gly Gln Tyr Pro Thr Asn Arg Leu Ala
145                 150                 155                 160 ttc gcg ttc ttc gac gag gac aag tac aag aac gag ctg aag aac ggc    528
Phe Ala Phe Phe Asp Glu Asp Lys Tyr Lys Asn Glu Leu Lys Asn Gly
                165                 170                 175 agg ccc cgg tcc ggc gaa acg cgg gcg gag ttc gag ggg cgc gtc gcc    576
Arg Pro Arg Ser Gly Glu Thr Arg Ala Glu Phe Glu Gly Arg Val Ala
            180                 185                 190 aag gac agc ttc gac gag gcg aag ggg ttc cag cgg gcg cgt gac gtg    624
Lys Asp Ser Phe Asp Glu Ala Lys Gly Phe Gln Arg Ala Arg Asp Val
        195                 200                 205 gcg tcc gtc atg aac aag gcc ctg gag aac gcc cac gac gag ggg gcg    672
Ala Ser Val Met Asn Lys Ala Leu Glu Asn Ala His Asp Glu Gly Ala
210                 215                 220 tac ctc gac aac ctc aag aag gag ctg gcg aac ggc aac gac gcc ctg    720
Tyr Leu Asp Asn Leu Lys Lys Glu Leu Ala Asn Gly Asn Asp Ala Leu
225                 230                 235                 240 cgg aac gag gat gcc cgc tcc ccc ttc tac tcg gcg ctg cgg aac acg    768
Arg Asn Glu Asp Ala Arg Ser Pro Phe Tyr Ser Ala Leu Arg Asn Thr
                245                 250                 255 ccg tcc ttc aag gac cgc aac ggc ggc aat cac gac ccg tcc aag atg    816
Pro Ser Phe Lys Asp Arg Asn Gly Gly Asn His Asp Pro Ser Lys Met
            260                 265                 270 aag gcc gtc atc tac tcg aag cac ttc tgg agc ggc cag gac cgg tcg    864
Lys Ala Val Ile Tyr Ser Lys His Phe Trp Ser Gly Gln Asp Arg Ser
        275                 280                 285 ggc tcc tcc gac aag agg aag tac ggc gac ccg gag gcc ttc cgc ccc    912
Gly Ser Ser Asp Lys Arg Lys Tyr Gly Asp Pro Glu Ala Phe Arg Pro
290                 295                 300 gac cgc ggc acc ggc ctg gtc gac atg tcg agg gac agg aac att ccg    960
Asp Arg Gly Thr Gly Leu Val Asp Met Ser Arg Asp Arg Asn Ile Pro
305                 310                 315                 320 cgc agc ccc acc agc ccc ggc gag agt ttc gtc aat ttc gac tac ggc   1008
Arg Ser Pro Thr Ser Pro Gly Glu Ser Phe Val Asn Phe Asp Tyr Gly
                325                 330                 335 tgg ttc gga gcg cag acg gaa gcg gac gcc gac aag acc gta tgg acc   1056
Trp Phe Gly Ala Gln Thr Glu Ala Asp Ala Asp Lys Thr Val Trp Thr
            340                 345                 350 cac ggc aac cac tac cac gcg ccc aat ggc agc ctg ggt gcc atg cac   1104
His Gly Asn His Tyr His Ala Pro Asn Gly Ser Leu Gly Ala Met His
        355                 360                 365 gtg tac gag agc aag ttc cgc aac tgg tcc gac ggt tac tcg gac ttc   1152
Val Tyr Glu Ser Lys Phe Arg Asn Trp Ser Asp Gly Tyr Ser Asp Phe
370                 375                 380
```

```
gac cgc gga gcc tac gtg gtc acg ttc gtc ccc aag agc tgg aac acc     1200
Asp Arg Gly Ala Tyr Val Val Thr Phe Val Pro Lys Ser Trp Asn Thr
385                 390                 395                 400 gcc ccc gac aag gtg aca cag ggc tgg ccg tga                          1233
Ala Pro Asp Lys Val Thr Gln Gly Trp Pro
            405                 410
```

<210> SEQ ID NO 2
<211> LENGTH: 410
<212> TYPE: PRT
<213> ORGANISM: Streptoverticillum ladakanum

<400> SEQUENCE: 2

```
Met Ser Gln Arg Gly Arg Thr Leu Val Phe Ala Ala Leu Gly Ala Val
1               5                   10                  15

Met Cys Thr Thr Ala Leu Met Pro Ser Ala Gly Ala Ala Thr Gly Ser
                20                  25                  30

Gly Ser Gly Ser Gly Thr Gly Glu Glu Lys Arg Ser Tyr Ala Glu Thr
            35                  40                  45

His Arg Leu Thr Ala Asp Asp Val Asp Asp Ile Asn Ala Leu Asn Glu
        50                  55                  60

Ser Ala Pro Ala Ala Ser Ser Ala Gly Pro Ser Phe Arg Ala Pro Asp
65                  70                  75                  80

Ser Asp Glu Arg Val Thr Pro Pro Ala Glu Pro Leu Asp Arg Met Pro
                85                  90                  95

Asp Pro Tyr Arg Pro Ser Tyr Gly Arg Ala Glu Thr Ile Val Asn Asn
            100                 105                 110

Tyr Ile Arg Lys Trp Gln Gln Val Tyr Ser His Arg Asp Gly Arg Lys
        115                 120                 125

Gln Gln Met Thr Glu Glu Gln Arg Glu Trp Leu Ser Tyr Gly Cys Val
130                 135                 140

Gly Val Thr Trp Val Asn Ser Gly Gln Tyr Pro Thr Asn Arg Leu Ala
145                 150                 155                 160

Phe Ala Phe Phe Asp Glu Asp Lys Tyr Lys Asn Glu Leu Lys Asn Gly
                165                 170                 175

Arg Pro Arg Ser Gly Glu Thr Arg Ala Glu Phe Glu Gly Arg Val Ala
            180                 185                 190

Lys Asp Ser Phe Asp Glu Ala Lys Gly Phe Gln Arg Ala Arg Asp Val
        195                 200                 205

Ala Ser Val Met Asn Lys Ala Leu Glu Asn Ala His Asp Glu Gly Ala
210                 215                 220

Tyr Leu Asp Asn Leu Lys Lys Glu Leu Ala Asn Gly Asn Asp Ala Leu
225                 230                 235                 240

Arg Asn Glu Asp Ala Arg Ser Pro Phe Tyr Ser Ala Leu Arg Asn Thr
                245                 250                 255

Pro Ser Phe Lys Asp Arg Asn Gly Gly Asn His Asp Pro Ser Lys Met
            260                 265                 270

Lys Ala Val Ile Tyr Ser Lys His Phe Trp Ser Gly Gln Asp Arg Ser
        275                 280                 285

Gly Ser Ser Asp Lys Arg Lys Tyr Gly Asp Pro Glu Ala Phe Arg Pro
290                 295                 300

Asp Arg Gly Thr Gly Leu Val Asp Met Ser Arg Asp Arg Asn Ile Pro
305                 310                 315                 320

Arg Ser Pro Thr Ser Pro Gly Glu Ser Phe Val Asn Phe Asp Tyr Gly
                325                 330                 335
```

-continued

```
Trp Phe Gly Ala Gln Thr Glu Ala Asp Ala Asp Lys Thr Val Trp Thr
            340                 345                 350

His Gly Asn His Tyr His Ala Pro Asn Gly Ser Leu Gly Ala Met His
        355                 360                 365

Val Tyr Glu Ser Lys Phe Arg Asn Trp Ser Asp Gly Tyr Ser Asp Phe
    370                 375                 380

Asp Arg Gly Ala Tyr Val Val Thr Phe Val Pro Lys Ser Trp Asn Thr
385                 390                 395                 400

Ala Pro Asp Lys Val Thr Gln Gly Trp Pro
                405                 410
```

<210> SEQ ID NO 3
<211> LENGTH: 644
<212> TYPE: DNA
<213> ORGANISM: Streptoverticillium mobraense

<400> SEQUENCE: 3

```
ttcgacgagg agaagggctt ccagcgggcg cgtgaggtgg cgtccgtcat gaacagggcc    60
ctggagaacg cccacgacga gagcgcttac ctcgacaacc tcaagaagga actggcgaac   120
ggcaacgacg ccctgcgcaa cgaagacgcc cgttccccgt tctactcggc gctgcggaac   180
acgccgtcct tcaaggagcg gaacggaggc aatcacgacc cgtccaggat gaaggccgtc   240
atctactcga agcacttctg gagcggccag gaccggtcga gttcggccga caagaggaag   300
tacggcgacc cggacgcctt ccgccccgcc cgggcaccg gcctggtcga catgtcgagg   360
gacaggaaca ttccgcgcag ccccaccagc ccggtgagg gattcgtcaa tttcgactac   420
ggctggttcg cgcccagac ggaagcggac gccgacaaga ccgtctggac ccacggaaat   480
cactatcacg cgcccaatgg cagcctgggt gccatgcatg tctacgagag caagttccgc   540
aactggtccg agggttactc ggacttcgac cgcggagcct atgtgatcac cttcatcccc   600
aagagctgga acaccgcccc cgacaaggta aagcagggct ggcc                   644
```

<210> SEQ ID NO 4
<211> LENGTH: 3241
<212> TYPE: DNA
<213> ORGANISM: Streptoverticillium ladakanum
<220> FEATURE:
<221> NAME/KEY: CDS
<222> LOCATION: (683)..(1915)
<223> OTHER INFORMATION:

<400> SEQUENCE: 4

```
ggtaccggcg cggggcggga agcgggagtt cctccgcgaa gtcgaagtcc tccaaggcga    60
gtccaagcgc cttcccttgc ccgaggccag cgccgaccct gctgcgtcga tgacggacgc   120
aggcgcaccg agtcccgcgg tctcgctcgc cggagggga tgcggcggtg tccggcgccc   180
agccggattc cgctcctgtg acggagtggc cggttttgga gccgtggtgt tgccggggag   240
ttaactggga gacatgatca cttctcgtag cgacccgatc actcgtccgg gagtcgagaa   300
gtgttacgcc gaacccccatt ccgcaccatc accctgccg ccgtgaccgc ggccggcagt   360
ctgcctctcg ccgagagagc cacccggaga accgccggga cggggtccgc ttcaccgctc   420
cggtgacggc ttcgacgtaa cacgaccgcg ccgtcaccgg ccgtatccgg tacgcaccgc   480
atccccattc cgccgtgcgg ccgcggcctc ttcctcaccg ccgttaccgg cgcggcaccg   540
caggacgggc accgccgac gttatgcgcg gccactcgcc gcaacctcca ccccccgcgt   600
cgcactctgg catgccctcg ttccgcgagg ttcgccagat tcagccctt cgtcacgttc   660
```

```
gccaaggag ttgttgttct tc atg tcc caa cgc ggg aga act ctc gtc ttc         712
                        Met Ser Gln Arg Gly Arg Thr Leu Val Phe
                         1               5                  10 gcc gct ctc ggt gcg gtc atg tgc acc acc gcg tta atg ccg tcc gca         760
Ala Ala Leu Gly Ala Val Met Cys Thr Thr Ala Leu Met Pro Ser Ala
            15                  20                  25 ggc gcg gcc acc ggc agt ggc agt ggc agc ggc acc ggg gaa gag aag         808
Gly Ala Ala Thr Gly Ser Gly Ser Gly Ser Gly Thr Gly Glu Glu Lys
         30                  35                  40 agg tcc tac gcc gaa acg cac cgc ctg acg gcg gat gac gtc gac gac         856
Arg Ser Tyr Ala Glu Thr His Arg Leu Thr Ala Asp Asp Val Asp Asp
     45                  50                  55 atc aac gcg ctg aac gaa agc gct ccg gcc gct tcg agc gcc ggt ccg         904
Ile Asn Ala Leu Asn Glu Ser Ala Pro Ala Ala Ser Ser Ala Gly Pro
 60                  65                  70 tcc ttc cgg gcc ccc gac tcc gac gag cgg gtg act cct ccc gcc gag         952
Ser Phe Arg Ala Pro Asp Ser Asp Glu Arg Val Thr Pro Pro Ala Glu
75                  80                  85                  90 ccg ctc gac cgg atg ccc gac ccg tac cgg ccc tcg tac ggc agg gcc        1000
Pro Leu Asp Arg Met Pro Asp Pro Tyr Arg Pro Ser Tyr Gly Arg Ala
                 95                 100                 105 gag acg atc gtc aac aac tac ata cgc aag tgg cag cag gtc tac agc        1048
Glu Thr Ile Val Asn Asn Tyr Ile Arg Lys Trp Gln Gln Val Tyr Ser
            110                 115                 120 cac cgc gac ggc agg aaa cag cag atg acc gag gaa cag cgg gag tgg        1096
His Arg Asp Gly Arg Lys Gln Gln Met Thr Glu Glu Gln Arg Glu Trp
         125                 130                 135 ctg tcc tac ggt tgc gtc ggt gtc acc tgg gtc aac tcg ggc cag tat        1144
Leu Ser Tyr Gly Cys Val Gly Val Thr Trp Val Asn Ser Gly Gln Tyr
    140                 145                 150 ccg acg aac agg ctg gct ttc gcg ttc ttc gac gag gac aag tac aag        1192
Pro Thr Asn Arg Leu Ala Phe Ala Phe Phe Asp Glu Asp Lys Tyr Lys
155                 160                 165                 170 aac gag ctg aag aac ggc agg ccc cgg tcc ggc gaa acg cgg gcg gag        1240
Asn Glu Leu Lys Asn Gly Arg Pro Arg Ser Gly Glu Thr Arg Ala Glu
                175                 180                 185 ttc gag ggg cgc gtc gcc aag gac agc ttc gac gag gcg aag ggg ttc        1288
Phe Glu Gly Arg Val Ala Lys Asp Ser Phe Asp Glu Ala Lys Gly Phe
            190                 195                 200 cag cgg gcg cgt gac gtg gcg tcc gtc atg aac aag gcc ctg gag aac        1336
Gln Arg Ala Arg Asp Val Ala Ser Val Met Asn Lys Ala Leu Glu Asn
         205                 210                 215 gcc cac gac gag ggg gcg tac ctc gac aac ctc aag aag gag ctg gcg        1384
Ala His Asp Glu Gly Ala Tyr Leu Asp Asn Leu Lys Lys Glu Leu Ala
    220                 225                 230 aac ggc aac gac gcc ctg cgg aac gag gat gcc cgc tcg ccc ttc tac        1432
Asn Gly Asn Asp Ala Leu Arg Asn Glu Asp Ala Arg Ser Pro Phe Tyr
235                 240                 245                 250 tcg gcg ctg cgg aac acg ccg tcc ttc aag gac cgc aac ggc ggc aat        1480
Ser Ala Leu Arg Asn Thr Pro Ser Phe Lys Asp Arg Asn Gly Gly Asn
                255                 260                 265 cac gac ccg tcc aag atg aag gcc gtc atc tac tcg aag cac ttc tgg        1528
His Asp Pro Ser Lys Met Lys Ala Val Ile Tyr Ser Lys His Phe Trp
            270                 275                 280 agc ggc cag gac cgg tcg ggc tcc tcc gac aag agg aag tac ggc gac        1576
Ser Gly Gln Asp Arg Ser Gly Ser Ser Asp Lys Arg Lys Tyr Gly Asp
         285                 290                 295 ccg gag gcc ttc cgc ccc gac cgc ggc acc ggc ctg gtc gac atg tcg        1624
Pro Glu Ala Phe Arg Pro Asp Arg Gly Thr Gly Leu Val Asp Met Ser
```

```
                300               305               310
agg gac agg aac att ccg cgc agc ccc acc agc ccc ggc gag agt ttc    1672
Arg Asp Arg Asn Ile Pro Arg Ser Pro Thr Ser Pro Gly Glu Ser Phe
315             320                 325                 330 gtc aat ttc gac tac ggc tgg ttc gga gcg cag acg gaa gcg gac gcc    1720
Val Asn Phe Asp Tyr Gly Trp Phe Gly Ala Gln Thr Glu Ala Asp Ala
                335                 340                 345 gac aag acc gta tgg acc cac ggc aac cac tac cac gcg ccc aat ggc    1768
Asp Lys Thr Val Trp Thr His Gly Asn His Tyr His Ala Pro Asn Gly
            350                 355                 360 agc ctg ggt gcc atg cac gtg tac gag agc aag ttc cgc aac tgg tcc    1816
Ser Leu Gly Ala Met His Val Tyr Glu Ser Lys Phe Arg Asn Trp Ser
        365                 370                 375 gac ggt tac tcg gac ttc gac cgc gga gcc tac gtg gtc acg ttc gtc    1864
Asp Gly Tyr Ser Asp Phe Asp Arg Gly Ala Tyr Val Val Thr Phe Val
    380                 385                 390 ccc aag agc tgg aac acc gcc ccc gac aag gtg aca cag ggc tgg ccg    1912
Pro Lys Ser Trp Asn Thr Ala Pro Asp Lys Val Thr Gln Gly Trp Pro
395                 400                 405                 410 tga tgtaagcggg gaggggaggg gaggcggagc atccggctcc cctccccacc         1965
gtcggctcta cagctcgtgg cccgtcgtgc tgtccacgtg gtccgggatc tcgccctcgt  2025
ggcggtcgcc cgtcgtcggg gtgcccgtgg gttcgaacat gaggatggag cgcccgggg   2085 aggacggctt gtgttcggtg cccttgggga ccacgaaggt gtcgcccttg tggagccgca  2145
cagcgcgttc cgtgccgtcg gggtcgcgga gggcgaggtc gaagcggccg tccaggacga  2205
ggaagaactc gtcggtgtcc tcgtgtacgt gccagatgtg ctcgccctgg gtgtgggcaa  2265
cgcggatgtc gtagtcgttc atgcgggcga cgatgcgcgg gctgtagacg tcgtcgaagg  2325
aggcgagagc cttggtgagg ttgacgggct cggtgttgtt catggtgtga gtctcggcgg  2385
gaggccgccg cggcgtcttg tacgttgctg tcacgccttg ttgctgtcac gcttcatga   2445 gggcgctcgc tccgaaggag acgtcaaagc ggtcgcacca gatgctgacg ctggtgtagc  2505
ggtcgaggtc caggtcccgt gggagggcgt agttctggtc gcccttgttg cctttcaggg  2565
agccgagact gacgtgggcg ccgtcgtcga agacgtgcca gccggcacgg cccggtttca  2625
ccggtgcgtc gctgaggagg accttcacgt ccgggccgtt gctcgtgtcg aggccctcca  2685
ggcggagggt gcggctgccg tccgggaggc ggaggacgcg gacggtgccg gaggtggtgt  2745
gttcgtggct gatgagggtg cccgtggcca gggtgcgggt ggcggcggtg ggcgccgcct  2805
cgtggaccgt ctcgttctgc cacagcttcc acggctggaa ccagtaggcc gccactccgg  2865
ccgccaggac cgcgacgccc agcgcccgg cggcgaacgg ccgccgccac caccgtcgta   2925
cctgtacgtg caccactgtc cgtctcccgt cgtctcgcgc catccggacc tgtatgaagc  2985
gcaacgtccg gggcggccgg atttctccca caaccggcac ggccacggga tcagtgcgtc  3045
acggcagcac cgccaccccg tccagttcca ccagtgcctc cccgtcccac agccgcaccg  3105
cgccgatcac cgccatcgcc gggtagtccc gccccgccag ccgccgccag acgcggccca  3165
gctccccggc gcacgcgcgg tacgccgcga cgtccgtcgt gtagaccgtg acgcgggcga  3225
ggtcggccgg ggtacc                                                  3241
```

<210> SEQ ID NO 5
<211> LENGTH: 410
<212> TYPE: PRT
<213> ORGANISM: Streptoverticillium ladakanum

<400> SEQUENCE: 5

-continued

```
Met Ser Gln Arg Gly Arg Thr Leu Val Phe Ala Ala Leu Gly Ala Val
 1               5                  10                  15
Met Cys Thr Thr Ala Leu Met Pro Ser Ala Gly Ala Ala Thr Gly Ser
                20                  25                  30
Gly Ser Gly Ser Gly Thr Gly Glu Glu Lys Arg Ser Tyr Ala Glu Thr
                35                  40                  45
His Arg Leu Thr Ala Asp Asp Val Asp Asp Ile Asn Ala Leu Asn Glu
            50                  55                  60
Ser Ala Pro Ala Ala Ser Ser Ala Gly Pro Ser Phe Arg Ala Pro Asp
 65                  70                  75                  80
Ser Asp Glu Arg Val Thr Pro Pro Ala Glu Pro Leu Asp Arg Met Pro
                85                  90                  95
Asp Pro Tyr Arg Pro Ser Tyr Gly Arg Ala Glu Thr Ile Val Asn Asn
                100                 105                 110
Tyr Ile Arg Lys Trp Gln Gln Val Tyr Ser His Arg Asp Gly Arg Lys
            115                 120                 125
Gln Gln Met Thr Glu Glu Gln Arg Glu Trp Leu Ser Tyr Gly Cys Val
            130                 135                 140
Gly Val Thr Trp Val Asn Ser Gly Gln Tyr Pro Thr Asn Arg Leu Ala
145                 150                 155                 160
Phe Ala Phe Phe Asp Glu Asp Lys Tyr Lys Asn Glu Leu Lys Asn Gly
                165                 170                 175
Arg Pro Arg Ser Gly Glu Thr Arg Ala Glu Phe Glu Gly Arg Val Ala
                180                 185                 190
Lys Asp Ser Phe Asp Glu Ala Lys Gly Phe Gln Arg Ala Arg Asp Val
                195                 200                 205
Ala Ser Val Met Asn Lys Ala Leu Glu Asn Ala His Asp Glu Gly Ala
            210                 215                 220
Tyr Leu Asp Asn Leu Lys Lys Glu Leu Ala Asn Gly Asn Asp Ala Leu
225                 230                 235                 240
Arg Asn Glu Asp Ala Arg Ser Pro Phe Tyr Ser Ala Leu Arg Asn Thr
                245                 250                 255
Pro Ser Phe Lys Asp Arg Asn Gly Gly Asn His Asp Pro Ser Lys Met
                260                 265                 270
Lys Ala Val Ile Tyr Ser Lys His Phe Trp Ser Gly Gln Asp Arg Ser
            275                 280                 285
Gly Ser Ser Asp Lys Arg Lys Tyr Gly Asp Pro Glu Ala Phe Arg Pro
            290                 295                 300
Asp Arg Gly Thr Gly Leu Val Asp Met Ser Arg Asp Arg Asn Ile Pro
305                 310                 315                 320
Arg Ser Pro Thr Ser Pro Gly Glu Ser Phe Val Asn Phe Asp Tyr Gly
                325                 330                 335
Trp Phe Gly Ala Gln Thr Glu Ala Asp Ala Asp Lys Thr Val Trp Thr
                340                 345                 350
His Gly Asn His Tyr His Ala Pro Asn Gly Ser Leu Gly Ala Met His
            355                 360                 365
Val Tyr Glu Ser Lys Phe Arg Asn Trp Ser Asp Gly Tyr Ser Asp Phe
            370                 375                 380
Asp Arg Gly Ala Tyr Val Val Thr Phe Val Pro Lys Ser Trp Asn Thr
385                 390                 395                 400
Ala Pro Asp Lys Val Thr Gln Gly Trp Pro
                405                 410
```